US010519194B2

(12) United States Patent
Kozlov et al.

(10) Patent No.: US 10,519,194 B2
(45) Date of Patent: Dec. 31, 2019

(54) REMOVAL OF FRAGMENTS FROM A SAMPLE CONTAINING A TARGET PROTEIN USING ACTIVATED CARBON

(71) Applicant: Merck Patent GmbH, Darmstadt (DE)

(72) Inventors: Mikhail Kozlov, Lexington, MA (US); Matthew T. Stone, Cambridge, MA (US); Romas Skudas, Mainz (DE); Kevin Galipeau, Westford, MA (US)

(73) Assignee: Merck Patent GmbH, Darmstadt (DE)

( * ) Notice: Subject to any disclaimer, the term of this patent is extended or adjusted under 35 U.S.C. 154(b) by 422 days.

(21) Appl. No.: 14/891,724

(22) PCT Filed: Apr. 4, 2014

(86) PCT No.: PCT/US2014/032937
§ 371 (c)(1),
(2) Date: Nov. 17, 2015

(87) PCT Pub. No.: WO2015/005960
PCT Pub. Date: Jan. 15, 2015

(65) Prior Publication Data
US 2016/0090399 A1    Mar. 31, 2016

Related U.S. Application Data

(60) Provisional application No. 61/845,422, filed on Jul. 12, 2013.

(51) Int. Cl.
| *C07K 1/22* | (2006.01) |
| *B01J 20/20* | (2006.01) |
| *B01D 15/26* | (2006.01) |
| *B01D 39/20* | (2006.01) |
| *C07K 16/00* | (2006.01) |

(52) U.S. Cl.
CPC .............. *C07K 1/22* (2013.01); *B01D 15/265* (2013.01); *C07K 16/00* (2013.01)

(58) Field of Classification Search
None
See application file for complete search history.

(56) References Cited

U.S. PATENT DOCUMENTS

| 6,127,526 | A | * | 10/2000 | Blank | .................. | C07K 16/065 |
| | | | | | | 530/413 |
| 6,177,548 | B1 | | 1/2001 | Wan et al. | | |
| 7,390,403 | B2 | | 6/2008 | Siwak | | |
| 8,123,940 | B2 | | 2/2012 | Sumian et al. | | |
| 2006/0281075 | A1 | | 12/2006 | Smith et al. | | |
| 2008/0058507 | A1 | | 3/2008 | Liu et al. | | |
| 2009/0149638 | A1 | | 6/2009 | Ley et al. | | |
| 2010/0150942 | A1 | | 6/2010 | Cantor | | |
| 2010/0234577 | A1 | | 9/2010 | Mazzola et al. | | |
| 2010/0322943 | A1 | | 12/2010 | Cantor | | |
| 2011/0263823 | A1 | | 10/2011 | Gagnon | | |
| 2011/0301333 | A1 | | 12/2011 | Potty et al. | | |
| 2012/0123002 | A1 | | 5/2012 | Shinohara et al. | | |
| 2012/0282654 | A1 | | 11/2012 | Yao et al. | | |
| 2013/0012689 | A1 | * | 1/2013 | Singh | .................. | B01D 15/3809 |
| | | | | | | 530/388.1 |
| 2013/0197200 | A1 | * | 8/2013 | Bian | .................... | B01D 15/362 |
| | | | | | | 530/388.1 |
| 2014/0046038 | A1 | | 2/2014 | Ishihara | | |
| 2015/0133636 | A1 | * | 5/2015 | Xenopoulos | ......... | B01D 15/362 |
| | | | | | | 530/387.1 |

FOREIGN PATENT DOCUMENTS

| CN | 103145813 | A | 6/2013 |
| EP | 0929579 | A1 | 7/1999 |
| EP | 1678208 | A2 | 7/2006 |
| EP | 2006305 | A2 | 12/2008 |
| EP | 2238154 | A1 | 10/2010 |
| EP | 2291388 | A1 | 3/2011 |
| EP | 2326658 | A1 | 6/2011 |
| EP | 2350127 | A1 | 8/2011 |
| EP | 2360183 | A1 | 8/2011 |
| EP | 2401065 | A1 | 1/2012 |
| EP | 2491055 | A2 | 8/2012 |
| EP | 2537862 | A1 | 12/2012 |
| JP | 2013-44748 | A | 3/2013 |
| WO | 2005044856 | A2 | 5/2005 |
| WO | 2013028330 | A2 | 2/2013 |
| WO | 2013028334 | A2 | 2/2013 |
| WO | 2013148389 | A1 | 10/2013 |
| WO | 2014/024514 | A1 | 2/2014 |

OTHER PUBLICATIONS

Ahn and Kopper "Pepsin digestion and adsorption of peanut proteins onto activated charcoal" Abstract of Papers, 237th ACS National Meeting (Year: 2009).*
Pete Gagnon "Polishing Methods for Monoclonal IgG Purification" pp. 491-505, from "Process Scale Bioseparation for the Biopharmaceutical Industry" Taylor & Francis Group, LLC (Year: 2007).*
Ebert et al., "Efficient Aggregate Removal from Impure Pharmaceutical Active Antibodies", 36 BioProcess International, Feb. 2011, 6 pages.
Gagnan, Pete, "Multiple Options for Removal of Antibody Aggregates by Apatite Chromatography", Ppt presentation at BioProcess International China, Beijing, Sep. 7-9, 2009, 32 pages.

(Continued)

*Primary Examiner* — Daniel E Kolker
*Assistant Examiner* — James L Rogers
(74) *Attorney, Agent, or Firm* — EMD Millipore Corporation

(57) ABSTRACT

The present invention provides novel and improved protein purification processes which incorporate certain types of carbonaceous materials and result in effective and selective removal, of protein, fragments without adversely affecting the yield of the desired protein product.

12 Claims, 4 Drawing Sheets

(56) References Cited

OTHER PUBLICATIONS

Gagnan et al., "New Insights into IgG Binding and Aggregate Removal with Hydroxyapatite", Ppt presentation at 8th Ube International Bioseparation Symposium, Nov. 29-31, 2008, 18 pages.

Gagnon, P., "Improved Antibody Aggregate Removal by Hydroxyapatite Chromatography in the Presence of Polyethylene Glycol", Journal of Immunological Methods, vol. 336, Issue 2, Jul. 31, 2008, pp. 222-228.

Guerrier et al., "A Dual Approach to the Selective Separation of Antibodies and their Fragments", Journal of Chromatography B: Biomedical Sciences and Applications, vol. 755, 2001, pp. 37-46.

Johnson et al., "Separation of Immunoglobulin M (IgM) Essentially Free of IgG from Serum for Use in Systems Requiring Assay of IgM-type Antibodies Without Interference from Rheumatoid Factor", Journal of Clinical Microbiology, vol. 12, No. 3, Sep. 1980, pp. 451-454.

McDonald et al., "Selective Antibody Precipitation Using Polyelectrolytes: A Novel Approach to the Purification of Monoclonal Antibodies", Biotechnology and Bioengineering, vol. 102, 2009, pp. 1141-1151.

International Search Report Received for PCT Application No. PCT/US2014/032937, dated Jul. 28, 2014, 4 pages.

Yigzaw et al., "Exploitation of the Adsorptive Properties of Depth Filters for Host Cell Protein Removal during Monoclonal Antibodypurification", Biotechnology Progress, American Instituteof Chemical Engineers, US, vol. 2, No. 1, Jan. 1, 2006, pp. 288-296.

\* cited by examiner

REMOVAL OF FRAGMENTS FROM A SAMPLE CONTAINING A TARGET PROTEIN USING ACTIVATED CARBON

FIELD OF THE INVENTION

The present invention relates to the use of activated carbon to remove fragments of a target protein from a sample.

BACKGROUND

The most commonly employed processes for purifying a protein, e.g., a monoclonal antibody typically employ an engineered cell line (e.g., a CHO cell line) capable of secreting the protein into the cell culture media. The media or cell culture feed containing the protein of interest is then subjected to a series of purification steps to separate the protein from various impurities, e.g., cells, cell debris, DNA, host cell proteins etc.

A typical purification process usually entails subjecting the cell culture feed or media containing the protein to a clarification step followed by subjecting the clarified cell culture feed to an antibody capture step (e.g., a Protein A affinity chromatography step), followed by a cation exchange bind/elute chromatography step and/or an anion exchange chromatography step.

While the various steps in the purification process are designed to remove impurities in the cell culture feed containing the protein, fragments of the protein which are undesirable, are typically difficult to remove as they share many of the same properties as the intact protein.

Activated carbon has previously been used in air filters (see, e.g., U.S. Pat. No. 6,413,303), gas purification (see, e.g., U.S. Pat. No. 7,918,923), decaffeination (see, e.g., U.S. Pat. No. 4,481,223), gold purification (see, e.g., U.S. Pat. No. 5,019,162), fuel purification (see, e.g., U.S. Publication No. 2006/0223705 A1), hemoperfusion (see, e.g., U.S. Pat. No. 4,048,064), treatment of poisonings and overdoses (see, e.g., U.S. Pat. No. 4,453,929), sewage treatment (see, e.g., U.S. Pat. No. 8,329,035), spill cleanup (see. e.g., U.S. Pat. No. 4,770,715), groundwater remediation (see, e.g., U.S. Pat. No. 6,116,816), capture of volatile organic compounds from automobile fuel systems (see, e.g., U.S. Pat. No. 7,044,112), chemical purification (see, e.g., U.S. Pat. No. 4,906,445), distilled alcoholic beverage purification (see. e.g., U.S. Publication No. US 2007/0248730 A1), decolorization of sugar (see, e.g., U.S. Pat. No. 2,082,425), respirators (see, e.g., U.S. Pat. No. 5,714,126), gas masks (see, e.g., U.S. Pat. No. 4,992,084), protective chemical warfare suits (see, e.g., U.S. Pat. No. 7,877,819), and water purification processes (see, e.g., U.S. Pat. No. 7,537,695).

In addition, activated carbon has been used to remove small molecule impurities, such as fatty acids and bilirubin, from serum albumin (see. e.g., Chen et al., J. Biol. Chem., 242: 173-181 (1967); Nakano el al., Anal Biochem., 129: 64-71 (1983); Nikolaev et al., Int. J. Art. Org., 14:179-185 (1991)). Activated carbon has also been used to remove pigments as well as host proteins, proteases, and ribonucleases during the purification of plant viruses (see, e.g., Price, Am. J. Botany, 33: 45-54 (1946); Corbett, Virology, 15:8-15 (1961); McLeana et al., Virology, 31: 585-591 (1967), U.S. Publication No. US 2006/0281075 A1). Additionally, activated carbon has also been described as being useful for removal of lower molecular weight plasmid fragments from plasmid DNA. See, Kim et al., J. Biosci. Bioeng. 110:608-613 (2010).

Further, U.S. patent application Ser. No. 13/565,463, filing date Aug. 2, 2012, incorporated by reference herein in its entirety, describes the use of activated carbon in combination with other media for removal of proteinaceous impurities (e.g., host cell proteins) and DNA from a sample containing a biomolecule of interest (e.g., an antibody).

Lastly, U.S. Provisional Patent Application Ser. No. 61/769,269, filing date Feb. 26, 2013, incorporated by reference herein, describes the use of activated carbon for the selective removal of a protein from a mixture of proteins by changing solution conditions.

SUMMARY OF THE INVENTION

The present invention is based, at least in part, on the surprising and unexpected discovery that activated carbon can be used for the removal of fragments from a sample containing a target protein (e.g., a monoclonal antibody) to be purified.

In some embodiments, a method for reducing the amount of fragments in a sample comprising a target protein to be purified is provided, the method comprising the steps of: (a) providing a sample comprising a target protein and fragments, wherein the fragments are present in an amount equal to or greater than at least 0.2% of the amount of the target protein; (b) contacting the sample with activated carbon; wherein the activated carbon binds the fragments; and (c) removing the activated carbon from the sample, thereby reducing the amount of the fragments in the sample.

In some embodiments, the target protein is an Fc-region containing protein. In other embodiments, the target protein is a non-immunoglobulin protein.

In some embodiments, the Fe-region containing protein is an antibody, e.g., a monoclonal antibody or a polyclonal antibody.

In some embodiments, the antibody is a monoclonal antibody. In other embodiments, the antibody is a polyclonal antibody.

In some embodiments, the fragments are in an amount equal to or greater than at least 0.5% of the amount of the target protein. In yet other embodiments, the fragments are in an amount equal to or greater than at least 1% of the amount of the target protein. In yet other embodiments, the fragments are in an amount equal to or greater than at least 2% of the amount of the target protein.

In some embodiments, a method of reducing the amount of antibody fragments in a sample comprising an antibody to be purified is provided, the method comprising the steps of: (a) providing a sample comprising an antibody and antibody fragments, wherein the antibody fragments are present in an amount equal to or greater than at least 0.2% of the amount of the antibody; (b) contacting the sample with activated carbon, wherein the activated carbon binds the antibody fragments; and (c) removing the activated carbon from the sample, thereby resulting in reducing the amount of fragments in the sample. In some embodiments, the antibody fragments are present in an amount equal to or greater than at least 0.5% of the amount of the antibody. In yet other embodiments, the antibody fragments are present in an amount equal to or greater than at least 1% of the amount of the antibody. In yet other embodiments, the antibody fragments are present in an amount equal to or greater than at least 2% of the amount of the antibody.

In some embodiments, antibody fragments include fragments that bind Protein A. In other embodiments, antibody fragments do not bind Protein A.

In some embodiments, the sample is an eluate collected from a Protein A chromatography column.

In some embodiments, the activated carbon is packed in a device. Exemplary devices include, e.g., a column (e.g., a chromatography column), a pod, a disc, a cartridge and a capsule.

In various embodiments, the methods described herein result in an increase in the purity of the target protein or the antibody (as the case may be). The purity of the target protein or the antibody may be increased, e.g., at least by 10%, or at least by 20%, or at least by 30%, or at least by 40%, or at least by 50%, or at least by 60%, or at least by 70%, or at least by 80%, or at least by 90%, or more, relative to a sample which is not contacted with activated carbon.

In some embodiments, the target protein-containing sample (or antibody containing sample) is a cell culture feed. In other embodiments, the cell culture is first clarified and/or purified prior to contacting with activated carbon. Clarification methods include, but are not limited to, centrifugation, settling, depth filtration, screen filtration, flocculation, use of a stimulus responsive polymer and pH change.

In some embodiments, the sample is subjected to one or more purification steps or methods prior to subjecting the sample to the methods described herein. Such purification steps or methods include but are not limited to, column and/or membrane chromatography operated in either bind and elute or flow-through mode; crystallization; two- and three-phase partitioning; and filtration.

DETAILED DESCRIPTION

Figure 1:
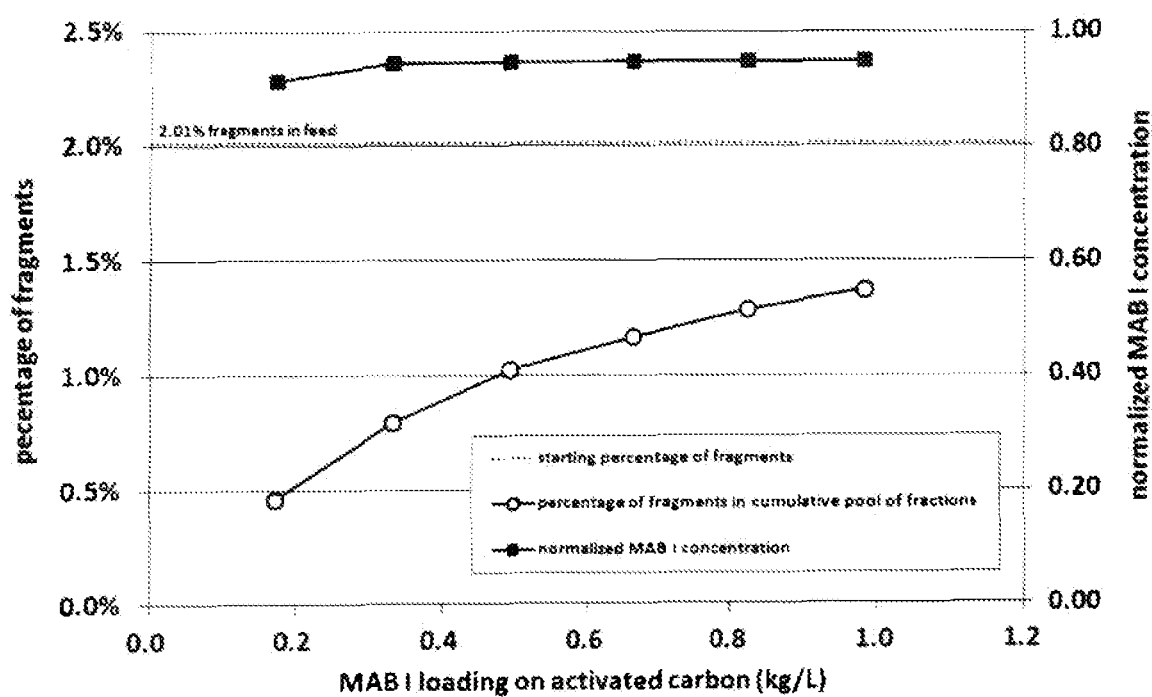
FIG. 1 is a graph depicting the results of a representative experiment to demonstrate the removal of monoclonal antibody fragments from a solution of monoclonal antibody by flowing through a column of activated carbon. A fragment spiked MAB I solution containing 5.01 mg/mL of MAB I with 2.01% of fragments was passed through a column packed with activated carbon. The X-axis depicts the mass of monoclonal antibody passed through the column divided by the volume of activated carbon (kg/L), the left Y-axis depicts the percentage of fragments in the cumulative fraction pool, and the right Y-axis depicts the concentration of monoclonal antibody in the cumulative fraction pool divided by the concentration of monoclonal antibody in the feed.

The present invention provides novel and improved processes for removing fragments from a sample containing a target protein to be purified.

Processes for purification of proteins, especially antibodies, are fairly well established. One of the key steps that is often used during purification of proteins (e.g., monoclonal antibodies) is a capture or affinity step which usually employs a ligand or compound that specifically binds the protein to be purified. For example, in case of monoclonal antibodies, such a step usually employs Protein A affinity chromatography.

While the capture step is useful for separating the target protein from a high percentage of various undesirable entities (e.g., impurities), the capture step is generally ineffective in the reducing the amount of fragments of the target protein in the fractions containing the target protein as many of the fragments interact with the affinity ligand and end up in the same fractions as the target protein. The fragments are undesirable impurities that are required to be removed from the purified protein, especially in case of therapeutic proteins which require regulatory approval.

Three types of media have been generally described for the removal of fragments. One of these is size exclusion chromatography, which separates fragments from the whole protein (e.g., a monoclonal antibody) based on differences in their hydrodynamic volumes. However, size exclusion chromatography is most commonly employed for analytical evaluation and is difficult to scale up for a practical purification of proteins, e.g., monoclonal antibodies. Another media that has been described as being useful for the removal of various impurities, including fragments, is ceramic hydroxyapatite (see, e.g., U.S. Patent Publication No. US20100234577). Ceramic hydroxyapatite is most often used to remove aggregated antibody impurities in a bind and elute mode. Lastly, a mixed mode ligand was described as being useful in separating fragments using hydrophobic charge induction chromatography in a bind and elute mode (see, e.g., J. Chromatogr. B.; 755: 37-46 (2001)).

Activated carbon has previously been used in water purification processes. In addition, activated carbon has been used to remove small molecule impurities, such as fatty acids and bilirubin, from serum albumin (see. e.g., Chen et al., J. Biol. Chem., 242: 173-181 (1967); Nakano et al., Anal Biochem., 129: 64-71 (1983); Nikolaev et al., Int. J. Art. Org., 14:179-185 (1991)). Activated carbon has also been used to remove pigments as well as host proteins, proteases, and ribonucleases during the purification of plant viruses (see, e.g., Price, Am. J. Botany, 33: 45-54 (1946); Corbett, Virology, 15:8-15 (1961); McLeana et al., Virology, 31: 585-591 (1967).

Accordingly, activated carbon has been reported to non-specifically bind to molecules in solution (e.g., impurities in a water sample).

Recently, activated carbon has been described as being used during protein purification processes. For example, U.S. patent application Ser. No. 13/565,463, filing date Aug. 2, 2012, incorporated by reference herein in its entirety, describes the use of activated carbon in combination with other media for removal of proteinaceous impurities (e.g., host cell proteins) and DNA from a sample containing a biomolecule of interest (e.g., an antibody). Further, U.S. Provisional Patent Application Ser. No. 61/769,269, filing date Feb. 26, 2013, incorporated by reference herein, describes the use of activated carbon for the selective removal of a protein from a mixture of proteins by changing solution conditions.

As demonstrated in the Examples herein, activated carbon can be used for reducing the amount of fragments of a target protein in a sample containing a target protein to be purified. Further, activated carbon can be used, as described herein, to increase the purity of a target protein in a solution containing the target protein and fragments of the protein, where removal of fragments using activated carbon results in increasing the purity of the target protein in the sample.

In order that the present disclosure may be more readily understood, certain terms are first defined. Additional definitions are set forth throughout the detailed description.

I. Definitions

The term "active carbon" or "activated carbon," as used interchangeably herein, refers to a carbonaceous material which has been subjected to a process to enhance its pore structure. Activated carbon is sometimes also referred to as activated charcoal. Activated carbons are porous solids with very high surface area. They can be derived from a variety of sources including coal, wood, coconut husk, nutshells, and peat. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

Typical activation processes involve subjecting a carbon source, such as, resin wastes, coal, coal coke, petroleum coke, lignites, polymeric materials, and lignocellulosic materials including pulp and paper, residues from pulp production, wood (like wood chips, sawdust, and wood flour), nut shell (like almond shell and coconut shell), kernel, and fruit pits (like olive and cherry stones) to a thermal process (e.g., with an oxidizing gas) or a chemical process (e.g., with phosphoric acid or metal salts, such as zinc chloride). An exemplary process involving chemical activation of wood-based carbon with phosphoric acid ($H_3PO_4$) is disclosed in U.S. Pat. No. Re. 31,093, which resulted in an improvement in the carbon's decolorizing and gas adsorbing abilities. Also, U.S. Pat. No. 5,162,286 teaches phosphoric acid activation of wood-based material which is particularly dense and which contains a relatively high (30%) lignin content, such as nut shell, fruit stone, and kernel. Phosphoric acid activation of lignocellulose material is also discussed in U.S. Pat. No. 5,204,310, as a step in preparing carbons of high activity and high density. The teachings of each of the patents listed in this paragraph are incorporated by reference herein in their entirety.

In contrast to most other adsorbing materials, activated carbon is believed to interact with molecules using relatively weak Van der Waals or London dispersion forces. Typical commercial activated carbon products exhibit a surface area of at least 300 $m^2/g$, as measured by the nitrogen adsorption based Brunauer-Emmett-Teller ("BET") method, which is method well known in the art.

Although, active or activated carbon has been previously employed in processes for purifying liquids and gases as well as for purifying a recombinantly expressed antibody from other impurities by binding to impurities such as host cell proteins (see, e.g., U.S. Publication Ser. No. 13/565, 463), it has not been previously employed for removing fragments (e.g., antibody fragments) from a sample.

In some embodiments, a sample is provided which includes the protein to be purified (e.g., a monoclonal antibody) and fragments in the amount equal to or greater than at least 0.2% of the amount of the target protein being purified. In other embodiments, the fragments are present in the amount equal to or greater than at least 0.5%, or equal to or greater than at least 1% of the amount of the target protein to be purified. In general, the purity of the target protein which remains after the removal of fragments increases, following the removal of fragments. The protein whose purity is increased is referred to as the target protein. The target protein may be an immunoglobulin or a non-immunoglobulin protein. In some embodiments, the target protein is an immunoglobulin protein, e.g., a monoclonal antibody.

The following are examples of proteins that can be purified according to the present invention. As discussed above, in some embodiments, the target protein is a monoclonal antibody. Other examples of target proteins include recombinant proteins which include, but are not limited to, recombinant human growth hormone, recombinant human insulin, recombinant follicle-stimulating hormone, recombinant factor VII (anti-hemophilic factor), recombinant human erythropoietin, recombinant granulocyte colony-stimulating factor, recombinant alpha-galactosidase a, recombinant iduronidase, recombinant galsulfase, recombinant dornase alfa, recombinant tissue plasminogen activator, recombinant human interferons, recombinant insulin-like growth factor 1, and recombinant asparaginase.

In other embodiments of this invention, target proteins are proteins derived from human blood or other physiological fluids. Examples of such proteins include, but not limited to, immunoglobulins G and M. Factor VII, Factor IX, anti-thrombin III, and alpha-1-antitrypsin.

The term "immunoglobulin," "Ig" or "IgG" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains". "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies).

The terms "Fc region" and "Fc region containing protein" mean that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $C_{H2}/C_{H3}$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

As discussed above, in some embodiments, a target protein is an Fc region containing protein, e.g., an immunoglobulin. In some embodiments, an Fc region containing protein is a recombinant protein which includes the Fc region of an immunoglobulin fused to another polypeptide or a fragment thereof.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal.

The term "monoclonal antibody" or "Mab," as used interchangeably herein, refers to an antibody obtained from a population of substantially homogeneous antibodies, i.e., the individual antibodies in the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991). Monoclonal antibodies may also be referred to as "MAbs" or "mabs" or "mAbs" or "MABs."

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5$^{th}$ Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta. Curr. Op. Struct. Biol. 2:593-596 (1992).

The term "fragment" or "fragments," as used herein, is an impurity that is composed of part a target protein and has a mass less than that of the target protein. The breakage of chemical bonds in the target protein results in the formation of one or more fragments. Incorrect or incomplete synthesis of the target protein may also result in fragments. Fragments are common impurities requiring removal during the purification of a target protein. They are difficult impurities to separate from the target protein because they often have properties very similar to the target protein, such as their hydrophobicity and isoelectric point. For example, if affinity chromatography is employed for the capture of a target protein, then the fragments containing the binding domain for the affinity ligand will also be captured and must be removed in later steps.

The term "solution," "composition" or "sample," as used herein, refers to a mixture of at least one target protein to be purified and fragments of the target protein present in an amount equal to or greater than at least 0.2% of the amount of the target protein. In some embodiments, the sample comprises cell culture feed, for example, feed from a mammalian cell culture (e.g., CHO cells) containing a target protein (e.g., a monoclonal antibody). In some embodiments, the sample comprises a cell culture feed which has been subjected to clarification. In a particular embodiment, the sample comprises an eluate from an affinity chromatography column (e.g., Protein A affinity chromatography column). Samples also encompass non-mammalian expression systems used for producing a protein of interest or target protein.

The term "non-mammalian expression systems," as used herein, refers to all host cells or organisms employed to generate therapeutic proteins, where the host cells or organisms are of non-mammalian origin. Examples of non-mammalian expression systems used for producing a protein of interest or target protein include yeast such as, *Saccharomyces cerevisiae* and *Pichia pastoris*, bacteria such as *Escherichia coli, Bacillus megaterium, Brevibacillus choshinensis*, insect cells such as *Spodoptera fugiperda* cells, Baculovirus infected insect cells, and algae cells.

The terms "protein of interest" and "target protein," as used interchangeably herein, refer to a protein or polypeptide, which is to be purified from a mixture of the target protein and fragments of the protein. In a particular embodiment, the target protein is an immunoglobulin.

The term "Protein A" or "ProA," as used interchangeably herein, encompasses Protein A recovered from a native source thereof (e.g., *Staphylococcus aureus*), Protein A produced synthetically (e.g., by peptide synthesis or by recombinant techniques), and fragments and variants thereof which retain the ability to bind proteins which have a $CH_2/CH_3$ region, such as an Fc region. Protein A can be purchased commercially from Repligen, Pharmacia, EMD Millipore and Fermatech. Protein A is generally immobilized on a solid phase support material. The term "ProA" also refers to an affinity chromatography resin or column containing chromatographic solid support matrix to which Protein A is covalently attached.

The term "purifying," "increasing the purity," "separating," or "isolating," as used interchangeably herein, refer to increasing the ratio of target protein to fragments of the target protein by selectively removing the fragments using the methods described herein. Typically, the purity of the target protein is increased by 50%, or by 60%, or by 70%, or by 80%, or by 90% or more, following removal of fragments in the sample containing the target protein.

As used herein, the term "remove," "removing," "removal," "reduce," "reducing" or "reduction," as used interchangeably herein, refer to lowering the amount of fragments in a sample which contains a target protein to be purified as well as fragments of the target protein in an amount equal to or greater than at least 0.2% of the amount of the target protein, using the methods described herein. In some embodiments, a sample contains fragments in an amount equal to or greater than at least 0.5% of the amount of the target protein. In other embodiments, s sample contains fragments in an amount equal to or greater than at least 1% of the amount of the target protein, or equal to or greater than at least 2% of the amount of the target protein. As demonstrated herein, activated carbon selectively binds the fragments and the level of fragments in the sample is reduced upon the removal of activated carbon from the sample, which is bound to the fragments.

The terms "selectively remove," "selectively removed," and "selective removal," as used interchangeably herein, refer to the ability of activated carbon to specifically bind fragments of a target protein in a sample containing the target protein to be purified and fragments of the target protein, in an amount equal to or greater than at least 0.2% of the amount of the target protein. Accordingly, while the activated carbon binds to fragments of the target protein, it does not bind to the target protein itself, thereby resulting in selective removal of the fragments from the sample following removal of the activated carbon from the sample.

The terms "clarify," "clarification," and "clarification step," as used herein, refers to a process step for removing suspended particles and or colloids, thereby to reduce turbidity, of a target protein containing solution, as measured in NTU (nephelometric turbidity units). Clarification can be achieved by a variety of means, including centrifugation or filtration. Centrifugation could be done in a batch or continuous mode, while filtration could be done in a normal flow (e.g. depth filtration) or tangential flow mode. In processes used in the industry today, centrifugation is typically followed by depth filtration intended to remove insoluble impurities, which may not have been removed by centrifugation. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation.

The terms "flow-through process," "flow-through mode," and "flow-through chromatography," as used interchangeably herein, refer to a product separation technique in which at least one product in a sample is intended to flow through a carbonaceous media, while at least one potential component binds to the carbonaceous media (e.g., activated carbon).

The sample intended to flow through is generally referred to as the "mobile phase." The "flow-through mode" is generally an isocratic operation (i.e., a process during which the composition of the mobile phase is not changed). The media used for flow-through is usually pre-equilibrated with the same buffer solution that contains the target protein molecule. After purification, the media can be flushed with additional quantity of the same buffer to increase the product recovery.

The term "buffer" refers to a solution that resists changes in pH by the action of its acid-base conjugate components. Various buffers which can be employed in the methods described herein are described in Buffers. A Guide for the Preparation and Use of Buffers in Biological Systems, Gueffroy, D., ed. Calbiochem Corporation (1975). Different buffers maintain different ranges of pH, for example phosphate buffer is usually used for pH between 6.0 and 8.0, while for a higher pH, a borate buffer can be used, and for lower pH, a carbonate buffer can be used. Persons of ordinary skill in the art will be able to readily identify a suitable buffer to use, depending on the pH to be maintained. Non-limiting examples of buffers that can be used in the methods according to the present invention include MES, MOPS, MOPSO, Tris, HEPES, phosphate, acetate, citrate, succinate, carbonate, borate, and ammonium buffers, as well as combinations of these.

The term "wash buffer" or "equilibration buffer" are used interchangeably herein, refers to a buffer used to wash or re-equilibrate the carbonaceous material (e.g., activated carbon) prior to contacting a sample with the carbonaceous material.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

II. Exemplary Carbonaceous Materials for Use in the Methods Described Herein

In methods according to the present invention, certain carbonaceous materials such as, activated carbon, are used for selective removal of fragments. Activated carbon can be described as a porous solid with a very high surface area. In some embodiments, activated carbon comprises activated charcoal. Activated carbon can be derived from a variety of sources including, but not limited to, coal, wood, coconut husk, nutshells, and peat. Activated carbon can be produced from these materials by physical activation involving heat under a controlled atmosphere or by chemical activation using strong acids, bases, or oxidants. The activation processes produce a porous structure with a high surface area that gives activated carbon a greater capacity for impurity removal. Activation processes can be modified to control the acidity of the surface.

Activated carbon is available from a wide variety of commercial sources and comes in a number of grades and formats. Some of the commercial suppliers of activated carbon include companies such as MeadWestVaco Corp., Richmond, Va., USA; Norit Americas Inc., Marshall, Tex. USA; Calgon Carbon Corp., Pittsburgh, Pa., USA.

In some embodiments described herein, activated carbon is incorporated in a cellulose-containing fibrous media, as described herein.

Commercially available activated carbon materials that may be employed in the methods according to the present invention include, but are not limited to, Nuchar HD activated carbon (MeadWestVaco Corporation, Richmond, Va., USA); Nuchar SA 20 (MeadWestVaco Corporation, Richmond, Va., USA); Nuchar SN (MeadWestVaco Corporation, Richmond, Va., USA); Nuchar WV-B 30 (MeadWestVaco Corporation, Richmond, Va., USA); RGC Powder activated carbon (MeadWestVaco Corporation, Richmond, Va., USA); Norit Darco KB-G activated carbon (Norit Americas Inc., Marshall, Tex., USA); Norit COP Super activated carbon (Norit Americas Inc., Marshall, Tex., USA); Norit A Supra USP (Norit Americas Inc., Marshall, Tex., USA); Norit E Supra USP (Norit Americas Inc., Marshall, Tex., USA); Norit C GRAN (Norit Americas Inc., Marshall, Tex., USA); Norit SX Ultra (Norit Americas Inc., Marshall, Tex., USA); and Chemviron Pulsorb PGC activated carbon (Chemviron Carbon. Feluy, Belgium).

Two major formats of activated carbon are powdered and granular. Powdered activated carbon contains small and usually less than 1 mm diameter particles, and is most commonly used for purification of liquids. Granular activated carbon has a larger particle size and consequently a smaller surface area, so it is preferred for use in gas purification where the rate of diffusion is faster.

An important consideration for safety with use of activated carbon in consumer applications (such as water, food, beverage, and pharmaceutical purification) is reduction and control of extractable compounds. Activated carbon intended for drinking water and food contact applications is usually made in compliance with safety standard ANSI/NSF Standard 61 that covers all indirect additives to water. Also, ASTM standard test method D6385 describes determining acid extractable content in activated carbon by ashing and could be used to study and minimize the level of extractables from activated carbon.

A range of activated carbon types is available for various applications. For example, MeadWestVaco Corp. supplies at least twelve types of powdered activated carbon that vary by their capacity, surface acidity, pore accessibility to target molecules, and intended application. It is generally desirable to maximize the capacity of activated carbon for impurity removal.

III. Methods of Determining the Amount of Fragments in a Sample

General techniques to determine the amount of fragments of a target protein in a sample include several different analytical chromatography processes. Size exclusion or gel permeation chromatography separates fragments from the target protein based on differences in their hydrodynamic volume. Reverse Phase HPLC and hydrophobic interaction chromatography (HIC) separates fragments from the target protein based on differences in their hydrophobicity. Anion exchange (AEX) and cation exchange (CEX) chromatography separates fragments from the target protein based on differences in the amount of charge. Mixed mode chromatography separates fragments from the target protein based on differences in both their amount of charge and their hydrophobicity.

The relative amount of proteins in a solution recovered from a chromatography column is typically determined using an in line UV detector although other types of in line detectors, such as refractive index detector, fluorescence detector, might also be employed. The different peaks in the resulting chromatogram are integrated to determine the areas of the target protein peak and the peaks corresponding to fragments of the target protein. The percentage of fragments in the sample is then calculated by dividing the sum of the area of all fragment peaks by the sum of the area of the target protein peak and the area of the all fragment peaks.

General techniques to determine the amount of fragments in a sample containing a target protein also include several different gel electrophoresis analytical techniques, such as SDS polyacrylamide gel (PAGE) electrophoresis, free flow electrophoresis, electrofocusing, isotachophoresis, affinity electrophoresis, immunoelectrophoresis, counterelectrophoresis, and capillary electrophoresis. The amount of protein in a section of the gel is then visualized, often using a stain. The intensity of the stained spots are quantified and the percentage of fragments in the sample is then calculated by dividing the intensity of the fragment peaks by the sum of the intensity of the target protein peak and the intensity of the fragment peaks.

IV. Use of Carbonaceous Material in Removal of Fragments

One general procedure which may be used for selectively removing fragments from a sample containing a target protein is described below.

In some embodiments, the fragment to be selectively reduced from a solution of the target protein using the methods described herein by static treatment of the solution with activated carbon. In this embodiment the activated carbon is added either in dry form or suspended in solution to the solution containing the target protein and the fragments to be removed. The solution is then allowed to interact with the activated carbon for a period of time up to 48 hours. The activated carbon is preferably kept suspended within the solution in order to maximize the rate of protein impurity adsorption. The solution can be agitated by movement of the solution container or stirring the solution with a magnetic stir bar or stirring the solution with a mechanical agitator.

The activated carbon is then separated out from the solution, where the activated carbon is bound to the fragments to be selectively removed. The bound activated carbon can be separated by filtering the solution and recovering the solution filtrate. Alternatively, the bound activated carbon can be separated by centrifuging the solution or allowing the bound activated carbon to settle and recovering the supernatant solution. If any particles remain in the supernatant after centrifugation or settling, they can be removed by filtration. The remaining solution contains reduced levels of fragments which are selectively removed.

In some embodiments, a chromatography device, e.g., a column, is loaded with an aqueous slurry of activated carbon. Activated carbon can also be loaded into a device, e.g., a column, as a dry powder and then wetted with an aqueous solution. However, sometimes it may be challenging to remove small air bubbles from in between the activated carbon particles when the column is dry packed. The column is then equilibrated with a buffer similar to the solution containing the target protein. Then the solution is subsequently passed through the activated carbon column at a flow-rate that results in a column residence time of between 15 secs and 10.0 mins. The solution that has passed through the column of activated carbon is then collected which does not contain or contains reduced levels of the fragments that were selectively removed using the activated carbon.

In various embodiments, the activated carbon which is bound to the fragments may be removed from the sample containing the target protein by filtration or centrifugation or a combination of both centrifugation and filtration. The initial level of fragments in the target protein solution may be determined by analytical chromatography (SEC, HIC, AEX, CEX, mixed mode) or analytical gel electrophoresis techniques (SDS PAGE, free flow electrophoresis, electrofocusing, isotachophoresis, affinity electrophoresis, immunoelectrophoresis, counterelectrophoresis, capillary electrophoresis).

This invention is further illustrated by the following examples which should not be construed as limiting. The contents of all references, patents and published patent applications cited throughout this application, as well as the Figures, are incorporated herein by reference.

EXAMPLES

Example 1

The Use of Activated Carbon for the Removal of Monoclonal Antibody Fragments Under Static Binding Conditions This representative example demonstrates that monoclonal antibody fragments can be selectively removed from a sample containing a monoclonal antibody by static treatment with activated carbon.

Solutions of two monoclonal antibodies, referred to as MAB I and MAB II, are prepared such that it contains approximately 1% of monoclonal antibody fragments and treated with activated carbon under static binding conditions, as described below.

Preparation of the MAB I and MAB II fragment spiked solutions began by digesting a portion of the monoclonal antibody with papain enzyme to produce the fragments. After digestion, the enzyme is inactivated by adding a solution of 0.3 M iodoacetate. The papain digested monoclonal antibody solutions are dialyzed into water with dialysis tubing (Standard RC Dialysis Trial Kits, Spectra/Por 1-3, 3.5K MWCO, 54 mm FLAT WIDTH, serial number: 132725. Spectrum Laboratories, Inc. Rancho Dominguez, Calif., 90220 USA) to remove buffer salts. The dialysis tubing is loaded with approximately 0.15 L of the papain digested monoclonal antibody solution and submerged in 4.0 L of water for 24 hours. The dialysis tubing is subsequently moved into a new container with 4.0 L of fresh water where it remains submerged for an additional 24 hours.

The fragment spiked MAB I stock solution is prepared from 0.5 mL of papain digested MAB I and 8.0 mL of undigested MAB I Protein A elution in 25 mM Tris at pH 7.0. The fragment spiked MAB II stock solution is prepared from 1.0 mL of papain digested MAB II, 8.0 mL of undigested MAB II in water, and 2.0 mL of 50 mM Tris at pH 7.0. The solutions are filtered through a 0.22 µm membrane (Stericup-GP 0.22 µm Millipore Express PLUS membrane, 250 mL, catalogue number: SCGPU02RE, EMDI) Millipore Corporation, Billerica, Mass. 01821, USA). The fragment spiked MAB I solution contains 5.52 mg/mL of MAB I with 1.06% of fragments and the fragment spiked MAB II solution contains 5.72 mg/mL of MAB II with 0.85% of fragments.

15 mL centrifuge tubes are loaded with 0 mg, 5 mg, or 10 mg of Nuchar HD activated carbon (MeadWestVaco Corporation, Richmond, Va., USA) for both monoclonal antibody solutions. 2.0 mL of the fragment spiked MAB I stock solution or the fragment spiked MAB II stock solution is added to the centrifuge tubes. The tubes are allowed to rotate for 20 hours. All the tubes are subsequently subjected to centrifugation and the supernatants are filtered through a 0.22 micron membrane (Millex Syringe Filter Units, Millex-GV, 0.22 µm, PVDF, 33 mm, gamma sterilized, catalogue number: SLGV033RB, EMD Millipore Corporation, Billerica, Mass., 01821, USA) to remove any activated carbon particles that might remain suspended in solution. The amount of the MAB I or MAB II remaining in the samples is determined using IgG quantification by Protein A HPLC. The percentage of fragments in the samples is determined by size exclusion chromatography (SEC).

As summarized in Table I below, this experiment demonstrates that static treatment of a sample containing a monoclonal antibody with activated carbon results in the selective removal of fragments of the monoclonal antibody, which are considered undesirable. As the amount of activated carbon added to the monoclonal antibody solution is increased, the percentage of fragments is reduced. Treatment of sample with 10 mg of activated carbon reduces the amount of fragments in the MAB I solution from 1.06% to below the limits of detection by SEC. Treatment with 10 mg of activated carbon reduces the amount of fragments in the MAB II solution from 0.85% to 0.15%. This data demonstrates that activated carbon can be used to selectively remove monoclonal antibody fragments from a sample under static binding conditions.

TABLE I

Recovery of monoclonal antibody and percentage of fragments after static treatment of MAB I and MAB II solutions with activated carbon. Note that 0.00% indicates that the percentage of fragments was below the limit of detection by SEC.

|  | activated carbon added (mg) | monoclonal antibody concentration | monoclonal antibody recovery | percentage of fragments |
|---|---|---|---|---|
| MAB I | 0 | 5.52 | — | 1.06% |
|  | 5 | 5.27 | 95% | 0.53% |
|  | 10 | 5.39 | 98% | 0.00% |
| MAB II | 0 | 5.72 | — | 0.85% |
|  | 5 | 5.36 | 94% | 0.42% |
|  | 10 | 5.34 | 93% | 0.15% |

Example 2

Removal of Monoclonal Antibody Fragments from a Sample Containing a Monoclonal Antibody by Flowing Through a Chromatography Column Packed with Activated Carbon This representative example demonstrates that monoclonal antibody fragments can be selectively removed from a sample containing a monoclonal antibody by flowing the sample through a chromatography column packed with activated carbon.

A solution of MAB I is prepared with approximately 2% of monoclonal antibody fragments and flowed through a chromatography column packed with activated carbon, as described below.

Preparation of the MAB I fragment spiked solution began by digesting a portion of the monoclonal antibody with papain enzyme to produce the fragments. After digestion the enzyme is inactivated by the addition of 0.3 M iodoacetate. The papain digested monoclonal antibody solutions are dialyzed into water with dialysis tubing (Standard RC Dialysis Trial Kits, Spectra/Por 1-3, 3.5K MWCO, 54 mm FLAT WIDTH, serial number: 132725, Spectrum Laboratories, Inc. Rancho Dominguez, Calif., 90220 USA) to remove buffer salts. The dialysis tubing is loaded with approximately 0.15 L of the papain digested monoclonal antibody solution and submerged in 4.0 L of water for 24 hours. The dialysis tubing is then moved into a new container with 4.0 L of fresh water where it remains submerged for an additional 24 hours.

The fragment spiked MAB I solution is prepared from 20 mL of papain digested MAB II solution in water and 160 mL of undigested MAB I Protein A elution in 25 mM Tris at pH 7.0. The solution is filtered through a 0.22 μm membrane (Stericup-GP 0.22 μm Millipore Express PLUS membrane, 250 mL, catalogue number: SCGPU02RE, EMD Millipore Corporation. Billerica, Mass. 01821, USA). The fragment spiked MAB I solution contains 5.01 mg/mL of MAB I with 2.01% of fragments.

A glass chromatography column (Omnifit Benchmark Column 10 mm/100 mm, 10 mm diameter, 100 mm length, SKU: 006BCC-10-10-AF, Diba Industries, Danbury, Conn. 06810, USA) is loaded with 200 mg of Nuchar HD activated carbon (MeadWestVaco Corporation, Richmond, Va., USA) slurried in water. The column is packed by flowing water through it, which results in a packed column volume of 0.8 mL. The column is equilibrated with 25 mM Tris at pH 7.0.

Next, 154 mL of the MAB I solution spiked with fragments is passed through the activated carbon column at 0.40 mL/min, giving a column residence time of 2.0 minutes. Six 25 mL fractions are collected. 10 mL of 25 mM Tris at pH 7.0 is subsequently passed through the column while an additional 10 mL fraction is collected. The amount of MAB I in the individual fractions as well as a proportionally pooled sample of all seven fractions is determined using IgG quantification by an HPLC system equipped with a Protein A affinity chromatography column ("Protein A HPLC"). The percentage of fragments in the individual fractions as well as a proportionally pooled sample of all seven fractions is determined by size exclusion chromatography (SEC).

As summarized in Table II below and FIG. 1, this experiment demonstrates that monoclonal antibody fragments can be selectively removed from a monoclonal antibody sample by flowing through a chromatography column packed with activated carbon.

TABLE II

Normalized concentration of MAB I and the percentage of fragments in the pooled fractions collected after passing through a column of activated carbon.

| loading of MAB I on activated carbon (kg/L) | normalized MAB I concentration in cumulative pool of fractions | percentage of fragments in cumulative pool of fractions |
|---|---|---|
| 0.17 | 0.91 | 0.46% |
| 0.33 | 0.94 | 0.79% |
| 0.49 | 0.95 | 1.02% |
| 0.66 | 0.95 | 1.17% |
| 0.82 | 0.95 | 1.29% |
| 0.98 | 0.95 | 1.37% |
| pool of fractions including rinse | 98% recovery | 1.24% |

Example 3

Selective Removal of Monoclonal Antibody Fragments that Bind Protein A from a Sample Containing a Monoclonal Antibody This representative example demonstrates that monoclonal antibody fragments that bind Protein A can be selectively removed from a sample containing a monoclonal antibody by flowing through a chromatography column packed with activated carbon.

A sample of MAB III is prepared with approximately 3.5% of monoclonal antibody fragments that bind Protein A. This sample is then flowed through a chromatography column packed with activated carbon, as described below.

Monoclonal antibody fragments that bind Protein A are prepared starting with 40 ml of 24.3 mg/ml MAB III solution, which is diluted with 100 mM sodium phosphate buffer and cysteine. Next, papain enzyme is added up to a final concentration of 0.11 mg/ml. The solution is incubated for 3 hours at 37° C. followed by inactivation of the papain enzyme by the addition of iodoacetate to give a final iodoacetate solution concentration of 20 mM. In order to ensure full enzyme inactivation, the solution is incubated for an additional hour at 37° C. before allowing to cool to room temperature. After digestion, the solution is concentrated by ultrafiltration/diafiltration using a polyethersulfone membrane (Pellicon XL Filter, cut off 30 KDa, EMD Millipore Corporation, Billerica, Mass. 01821). Next, the concentrated MAB III digest is subjected to buffer exchange into 20 mM PBS at pH 7.4. The concentrated MAB III digest at pH 7.4 is subjected to the Protein A column (ProSep® Ultra Plus, 10*100 mm, Merck KGaA, Darmstadt, Germany). The MAB III fragments that bind Protein A are eluted from the column with 100 mM glycine buffer at pH 2.9 after washing with 20 mM PBS buffer at pH 7.4. The pH of the eluted fraction is then increased to pH 5.4 by the addition a solution of 2.0 M Tris base.

The fragment spiked MAB III sample is prepared from 120 mL of MAB III solution at pH 7.0 and 12 mL of the MAB II fragment solution. The fragment spiked MAB III sample is filtered through a 0.22 µm membrane (Stericup-GP 0.22 µm Millipore Express PLUS membrane, 250 mL, catalogue number: SCGPU02RE, EMD Millipore Corporation. Billerica, Mass. 01821, USA). The fragment spiked MAB III solution contains 7.13 mg/mL of MAB III with 3.50% of fragments.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 250 mg of Nuchar HD activated carbon (MeadWestVaco Corporation, Richmond, Va., USA) slurried in water. The column is packed by flowing water through it, which results in a packed column volume of 1.0 mL. The column is equilibrated with 25 mM Tris at pH 7.0.

30.5 mL, of the MAB III solution spiked with fragments is passed through the activated carbon column at 0.30 mL/min, giving a residence time of 3.3 minutes in the activated carbon column. Seventeen 1.9 mL fractions are collected. The amount of MAB III in the individual fractions is determined using IgG quantification by Protein A HPLC. The percentage of fragments in the individual fractions is determined by size exclusion chromatography (SEC).

Figure 2:
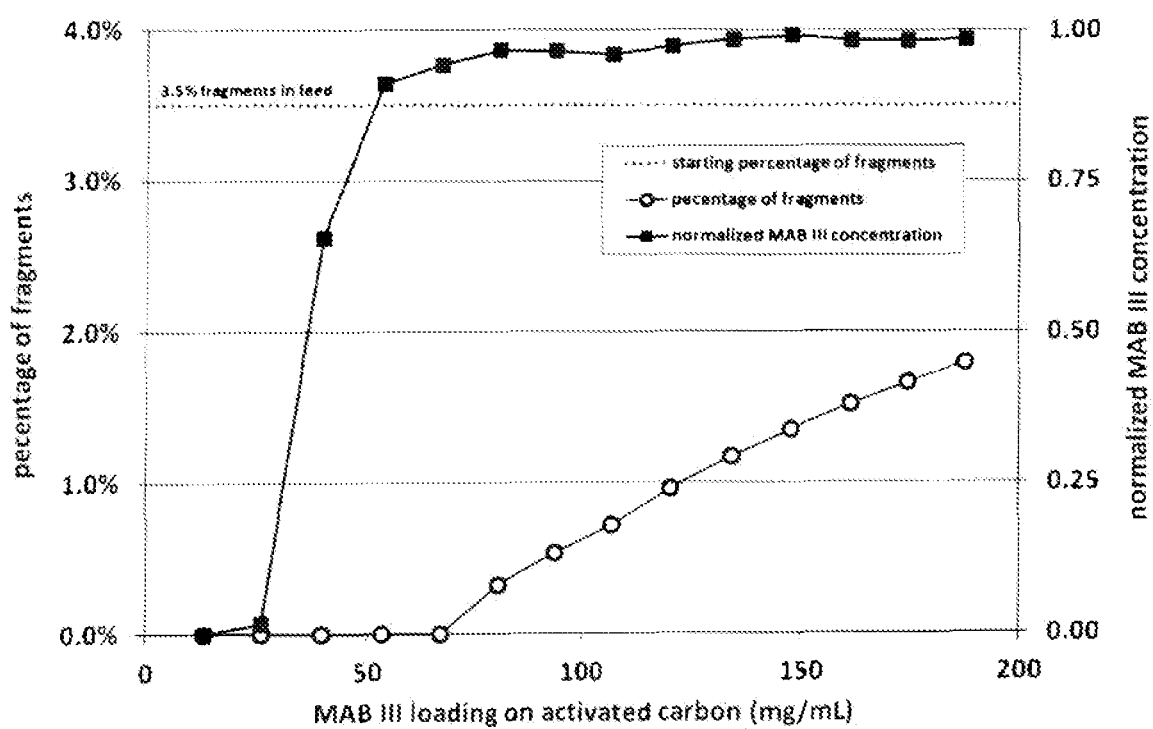
FIG. 2 is a graph depicting the results of a representative experiment to demonstrate the removal of monoclonal antibody fragments that bind Protein A from a solution of monoclonal antibody by flowing through a column of activated carbon. The fragment spiked MAB III solution containing 7.13 mg/mL of MAB III with 3.50% of fragments was passed through a column packed with activated carbon. The X-axis depicts the mass of monoclonal antibody passed through the column divided by the volume of activated carbon (mg/mL), the left Y-axis depicts the percentage of fragments in the monoclonal antibody collected in a specific column fraction, and the right Y-axis depicts the concentration of monoclonal antibody in a specific column fraction divided by the concentration of monoclonal antibody in the feed.

As summarized in Table III and FIG. 2, this experiment demonstrates that monoclonal antibody fragments that bind Protein A can be selectively removed from a monoclonal antibody containing sample by flowing through a chromatography column packed with activated carbon. This result demonstrates that activated carbon can be used to remove fragments that are commonly found and often difficult to remove as they end up in the same Protein A elution pool as the antibody being purified.

TABLE III

Concentration of MAB III and the percentage of monoclonal antibody fragments that bind Protein A in the fractions collected after passing the sample through a column of activated carbon.

| flow through fraction | mAb (mg/ml) | cumulative volume (ml) | mAb loading (mg/ml AC) | Percentage Fragments (%) |
|---|---|---|---|---|
| Feed | 7.13 | — | — | 3.50 |
| 2 | 0.00 | 1.9 | 13.3 | 0.00 |
| 3 | 0.12 | 3.7 | 26.4 | 0.00 |
| 4 | 4.66 | 5.6 | 39.8 | 0.00 |

TABLE III-continued

Concentration of MAB III and the percentage of monoclonal antibody fragments that bind Protein A in the fractions collected after passing the sample through a column of activated carbon.

| flow through fraction | mAb (mg/ml) | cumulative volume (ml) | mAb loading (mg/ml AC) | Percentage Fragments (%) |
|---|---|---|---|---|
| 5 | 6.49 | 7.5 | 53.3 | 0.00 |
| 6 | 6.72 | 9.4 | 66.8 | 0.00 |
| 7 | 6.89 | 11.3 | 80.2 | 0.32 |
| 8 | 6.88 | 13.1 | 93.5 | 0.53 |
| 9 | 6.84 | 15.0 | 106.9 | 0.72 |
| 10 | 6.94 | 16.9 | 120.3 | 0.96 |
| 11 | 7.02 | 18.8 | 134.2 | 1.17 |
| 12 | 7.07 | 20.7 | 147.5 | 1.35 |
| 13 | 7.01 | 22.6 | 161.0 | 1.52 |
| 14 | 7.01 | 24.5 | 174.4 | 1.66 |
| 15 | 7.02 | 26.4 | 187.9 | 1.79 |
| 16 | 3.80 | 28.4 | 202.1 | 1.06 |
| 17 | 0.15 | 30.4 | 216.4 | 0.07 |

Example 4

Removal of Monoclonal Antibody Fragments which do not Bind Protein A from a Sample Containing a Monoclonal Antibody This representative example demonstrates that monoclonal antibody fragments that do not bind Protein A can also be selectively removed from a sample containing a monoclonal antibody by flowing through a chromatography column packed with activated carbon.

A solution of MAB III is prepared with approximately 4.84% of monoclonal antibody fragments that do not bind Protein A and then flowed through a chromatography column packed with activated carbon, as described below.

Monoclonal antibody fragments that do not bind Protein A are prepared by starting with 40 ml of 24.3 mg/ml MAB III solution, which is diluted with 100 mM sodium phosphate buffer and cysteine. Next, papain enzyme is added up to a final concentration of 0.11 mg/ml. The solution is incubated for 3 hours at 37° C. followed by inactivation of the papain enzyme by the addition of iodoacetate, to give a final iodoacetate solution concentration of 20 mM. In order to ensure full enzyme inactivation, the solution is incubated for an additional hour at 37° C. before allowing to cool to room temperature. After digestion, the solution is concentrated by ultrafiltration/diafiltration using a polyethersulfone membrane (Pellicon XL Filter, cut off 30 KDa, EMD Millipore Corporation, Billerica, Mass. 01821). Next, the concentrated MAB III digest is subjected to buffer exchange into 20 mM PBS at pH 7.4. The concentrated MAB III digest at pH 7.4 is loaded on a Protein A column (ProSep® Ultra Plus, 10*100 mm, Merck KGaA, Darmstadt, Germany). Fragments that do not bind Protein A are isolated by flowing the concentrated MAB III digest through the Protein A column.

The fragment spiked MAB III solution is prepared from 150 mL of MAB III solution at pH 7.0 and 20 mL of the solution generated above containing MAB III fragments that do not bind Protein A. The fragment spiked MAB III stock solution is then filtered through a 0.22 µm membrane (Stericup-GP 0.22 µm Millipore Express PLUS membrane, 250 mL, catalogue number: SCGPU02RE, EMD Millipore Corporation. Billerica, Mass., 01821. USA). The fragment spiked MAB III solution contained 1.27 mg/mL of MAB III and 4.84% of fragments.

A glass chromatography column (Omnifit Benchmark Column 10 mm/100 mm, 10 mm diameter, 100 mm length, SKU: 006BCC-10-10-AF, Diba Industries, Danbury, Conn. 06810, US) is loaded with 250 mg of Nuchar HD activated carbon (MeadWestVaco Corporation. Richmond, Va., USA) slurried in water. The column is packed by flowing water through it, resulting in a packed column volume of 1.0 mL. The column is equilibrated with 25 mM TRIS at pH 7.0.

Next, 130.5 mL of the MAB III solution spiked with fragments is passed through the activated carbon column at 0.30 mL/min giving a residence time of 3.3 minutes in the activated carbon column. Thirty 4.5 mL fractions are collected. The amount of MAB III in the individual fractions is determined using IgG quantification by Protein A HPLC. The percentage of fragments in the individual fractions is determined by size exclusion chromatography (SEC).

Figure 3:
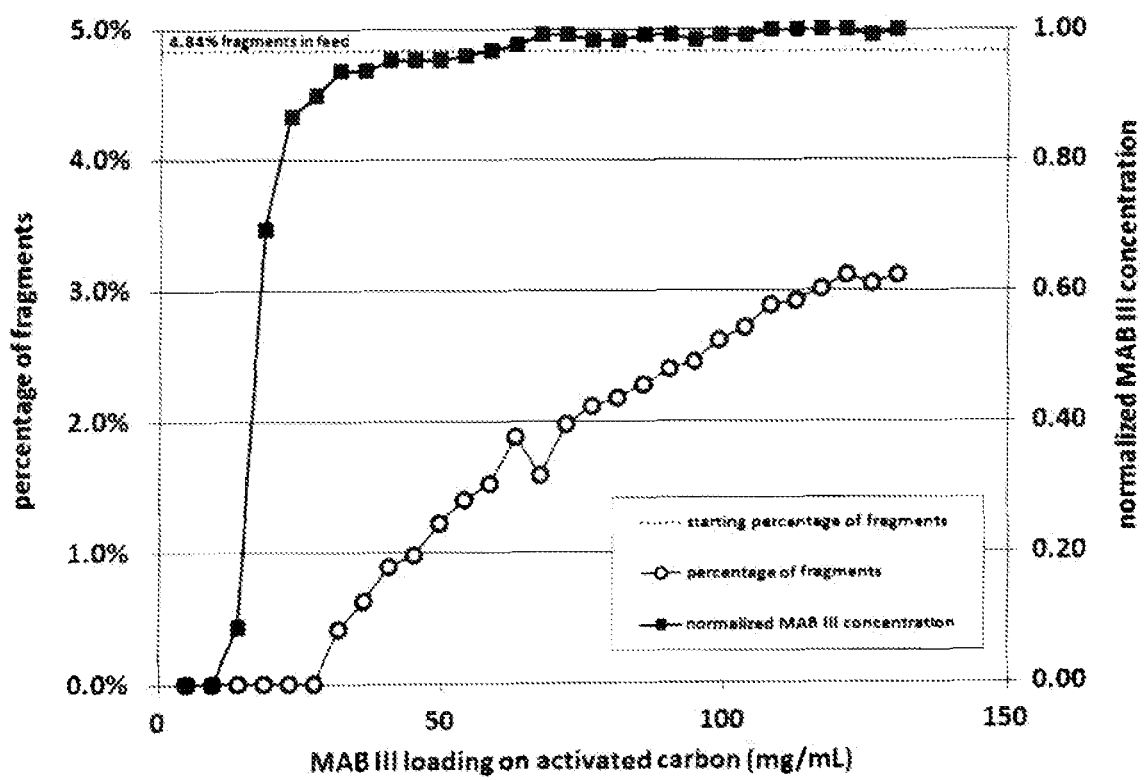
FIG. 3 is a graph depicting the results of a representative experiment to demonstrate the removal of monoclonal antibody fragments that do not bind Protein A from a solution of monoclonal antibody by flowing through a column packed with activated carbon. The fragment spiked MAB III solution containing 1.27 mg/mL of MAB III with 4.84% of fragments was passed through a column of activated carbon. The X-axis depicts the mass of monoclonal antibody passed through the column divided by the volume of activated carbon (mg/mL), the left Y-axis depicts the percentage of fragments in the monoclonal antibody collected in a specific column fraction, and the right Y-axis depicts the concentration of monoclonal antibody in a specific column fraction divided by the concentration of monoclonal antibody in the feed.

As summarized in Table IV and FIG. 3, this experiment demonstrates that monoclonal antibody fragments that do not bind Protein A can also be selectively removed from sample containing a monoclonal antibody by flowing through a chromatography column packed with activated carbon.

TABLE IV

Concentration of MAB III and the percentage of monoclonal antibody fragments that do not bind Protein A in the fractions collected after passing the sample through a column of activated carbon.

| flow through fraction | mAb (mg/ml) | cumulative volume (ml) | mAb loading (mg/ml) | fragment (%) |
| --- | --- | --- | --- | --- |
| feed | 1.27 | | | 4.84 |
| 2 | 0.00 | 4.5 | 6 | 0.00 |
| 3 | 0.00 | 9.0 | 11 | 0.00 |
| 4 | 0.11 | 13.5 | 17 | 0.00 |
| 5 | 0.88 | 18.0 | 23 | 0.00 |
| 6 | 1.10 | 22.5 | 28 | 0.00 |
| 7 | 1.14 | 27.0 | 34 | 0.00 |
| 8 | 1.19 | 31.5 | 40 | 0.42 |
| 9 | 1.19 | 36.0 | 46 | 0.63 |
| 10 | 1.21 | 40.5 | 51 | 0.89 |
| 11 | 1.21 | 45.0 | 57 | 0.98 |
| 12 | 1.21 | 49.5 | 63 | 1.22 |
| 13 | 1.22 | 54.0 | 68 | 1.40 |
| 14 | 1.23 | 58.5 | 74 | 1.52 |
| 15 | 1.24 | 63.0 | 80 | 1.88 |
| 16 | 1.26 | 67.5 | 85 | 1.59 |
| 17 | 1.26 | 72.0 | 91 | 1.98 |
| 18 | 1.25 | 76.5 | 97 | 2.12 |
| 19 | 1.25 | 81.0 | 103 | 2.18 |
| 20 | 1.26 | 85.5 | 108 | 2.28 |
| 21 | 1.26 | 90.0 | 114 | 2.40 |
| 22 | 1.25 | 94.5 | 120 | 2.46 |
| 23 | 1.26 | 99.0 | 125 | 2.62 |
| 24 | 1.26 | 103.5 | 131 | 2.72 |
| 25 | 1.27 | 108.0 | 137 | 2.89 |
| 26 | 1.27 | 112.5 | 142 | 2.92 |
| 27 | 1.27 | 117.0 | 148 | 3.01 |
| 28 | 1.27 | 121.5 | 154 | 3.12 |
| 29 | 1.26 | 126.0 | 159 | 3.05 |
| 30 | 1.27 | 130.5 | 165 | 3.12 |

Example 5

The Use of Different Types of Activated Carbon for the Removal of Monoclonal Antibody Fragments from a Sample Containing a Monoclonal Antibody Under Static Binding Conditions This representative example demonstrates that monoclonal antibody fragments can be selectively removed from a sample containing a monoclonal antibody by static treatment with different types of activated carbon.

Solutions of MAB II are prepared with approximately 1.7% of monoclonal antibody fragments and treated with one of three different types of activated carbon under static binding conditions, as described below.

Preparation of the MAB II fragment spiked solutions began by digesting a portion of the monoclonal antibody with papain enzyme to produce the antibody fragments. After digestion, the enzyme is inactivated by adding a solution of 0.3 M iodoacetate. The papain digested monoclonal antibody solutions were dialyzed into water with dialysis tubing (Standard RC Dialysis Trial Kits, Spectra/Por 1-3, 3.5K MWCO, 54 mm FLAT WIDTH, serial number: 132725, Spectrum Laboratories, Inc. Rancho Dominguez, Calif., 90220 USA) to remove buffer salts. The dialysis tubing is loaded with approximately 0.15 L of the papain digested monoclonal antibody solution and submerged in 4.0 L of water for 24 hours. The dialysis tubing is then moved into a new container with 4.0 L of fresh water where it remains submerged for an additional 24 hours.

A MAB II solution spiked with monoclonal antibody fragments is prepared from 18.0 ml, of papain digested MAB II, 72.0 mL of undigested MAB II in water, and 9.0 mL of 250 mM Tris at pH 7.0. The solution is then filtered through a 0.22 μm membrane (Stericup-GP 0.22 μm Millipore Express PLUS membrane, 250 mL, catalogue number: SCGPU02RE, EMD Millipore Corporation, Billerica, Mass., 01821. USA). The fragment spiked MAB II solution contains 7.86 mg/mL of MAB II and 1.72% of fragments.

15 mL centrifuge tubes are loaded with 5 mg or 10 mg of Nuchar HD activated carbon (MeadWestVaco Corporation, Richmond, Va., USA), Darco KB-G activated carbon (Norit Americas Inc., Marshall, Tex., USA), or CGP Super activated carbon (Norit Americas Inc., Marshall, Tex., USA). No media is added to an additional set of 15 mL centrifuge tubes that are used as a control. Then, 5.0 mL of the fragment spiked MAB II is added to the centrifuge tubes. The tubes are allowed to rotate for 20 hours. The tubes are then subjected to centrifugation and samples filtered through a 0.22 micron membrane (Millex Syringe Filter Units, Millex-GV, 0.22 μm, PVDF, 33 mm, gamma sterilized, catalogue number: SLGV033RB, EMD Millipore Corporation, Billerica, Mass., 01821, USA) to remove any activated carbon particles that might remain suspended in solution. The amount of the MAB II remaining in the samples is determined using IgG quantification by Protein A HPLC. The percentage of fragments in the samples is determined by size exclusion chromatography (SEC).

As summarized in Table V below, this experiment demonstrates that monoclonal antibody fragments can be selectively removed from a sample containing the monoclonal antibody by treatment with different types of activated carbon under static binding conditions. As the amount of activated carbon added to the monoclonal antibody solution is increased, the percentage of fragments present is reduced. The data indicates that different types of activated carbon can be used to selectively remove monoclonal antibody fragments from a sample containing a monoclonal antibody under static binding conditions.

TABLE V

Recovery of monoclonal antibody and percentage of fragments after static treatment of MAB II solutions with three different types of activated carbon.

| media | amount of media | MAB II concentration | MAB II recovery | percentage of fragments |
|---|---|---|---|---|
| average of two controls | — | 7.86 | — | 1.72 |
| Nuchar HD | 10 mg | 7.75 | 99% | 0.73 |
| Nuchar HD | 20 mg | 7.60 | 97% | 0.34 |
| CGP Super | 10 mg | 7.53 | 96% | 1.08 |
| CGP Super | 20 mg | 7.57 | 96% | 0.66 |
| Darco KB-G | 10 mg | 7.73 | 98% | 1.01 |
| Darco KB-G | 20 mg | 7.76 | 99% | 0.47 |

Example 6

Use of Activated Carbon for the Removal of Monoclonal Antibody Fragments from a Sample Containing a Monoclonal Antibody at Neutral and Acidic pH Under Static Binding Conditions This representative example demonstrates that monoclonal antibody fragments can be selectively removed from a sample containing a monoclonal antibody by static treatment at both acidic and neutral pH solution conditions using activated carbon.

Solutions of MAB II are prepared with approximately 1.72% of monoclonal antibody fragments at pH 4.1 or pH 7.5 and treated with activated carbon under static binding conditions.

Preparation of the MAB II fragment spiked solutions began by digesting a portion of the monoclonal antibody with papain enzyme to produce the fragments. After digestion, the enzyme is inactivated by adding a solution of 0.3 M iodoacetate. The papain digested monoclonal antibody solutions are dialyzed into water with dialysis tubing (Standard RC Dialysis Trial Kits, Spectra/Por 1-3, 3.5K MWCO, 54 mm FLAT WIDTH, serial number: 132725, Spectrum Laboratories, Inc. Rancho Dominguez, Calif., 90220 USA) to remove buffer salts. The dialysis tubing is loaded with approximately 0.15 L of the papain digested monoclonal antibody solution and submerged in 4.0 L of water for 24 hours. The dialysis tubing is subsequently moved into a new container with 4.0 L of fresh water where it remains submerged for an additional 24 hours.

The fragment spiked MAB II solution is prepared from 18 mL of papain digested MAB II in water, 72 mL of undigested MAB II in water, and 9 mL of 250 mM Tris at pH 7.0. A portion of this solution is lowered to pH 4.1 by the addition of 3.0 M acetic acid. The solution pH is raised to 7.5 by the addition of Tris base. The solutions are then filtered through a 0.22 µm membrane (Stericup-OP 0.22 µm Millipore Express PLUS membrane, 250 mL, catalogue number: SCGPU02RE, EMD Millipore Corporation, Billerica, Mass., 01821, USA). The fragment spiked MAB II solution at pH 4.1 contains 7.88 mg/mL of MAB II with 1.76% of fragments and the fragment spiked MAB II solution at pH 7.5 contained 7.78 mg/mL of MAB II with 1.72% of fragments.

15 mL centrifuge tubes are loaded with 20 mg of Nuchar HD activated carbon (MeadWestVaco Corporation. Richmond, Va., USA). No activated carbon is added to a second set of 15 mL centrifuge tubes that are used as a control. 5.0 mL of the fragment spiked MAB II stock solutions at pH 4.1 or pH 7.5 are added to the appropriate centrifuge tubes. The tubes are allowed to rotate for 24 hours. The solutions are filtered through a 0.22 micron membrane (Millex Syringe Filter Units, Millex-GV, 0.22 µm, PVDF, 33 mm, gamma sterilized, catalogue number: SLGV033RB, EMD Millipore Corporation, Billerica, Mass., 01821, USA) to remove any particles that might remain suspended in solution. The concentration of the MAB II remaining in the solutions is determined by measuring the absorbance at 280 nm. The percentage of fragments in the samples is determined by size exclusion chromatography (SEC).

As summarized in Table VI below, this experiment demonstrates that monoclonal antibody fragments can be selectively removed from a monoclonal antibody solution by static treatment with activated carbon at both neutral and acidic pH conditions.

TABLE VI

Recovery of monoclonal antibody and percentage of fragments after static treatment of MAB II solution with activated carbon at a neutral pH of 7.5 or an acidic pH of 4.1.

| | solution pH | amount of activated carbon added | antibody recovery | fragment percentage |
|---|---|---|---|---|
| Control | 7.5 | 0 | — | 1.76 |
| Control | 4.1 | 0 | — | 1.72 |
| activated carbon | 7.5 | 20 mg | 89% | 0.55 |
| activated carbon | 4.1 | 20 mg | 91% | 0.29 |

Example 7

Use of Activated Carbon for the Removal of Monoclonal Antibody Fragments from a Sample Containing a Monoclonal Antibody Over a pH Range of 4.0 to 9.0 at Both Low and High Conductivities Under Static Binding Conditions This representative example demonstrates that monoclonal antibody fragments can be selectively removed from a solution of a monoclonal antibody by static treatment using activated carbon over a pH range from 4.0 to 9.0 at both low and high solution conductivities.

Solutions of MAB II are prepared containing between 1.49% and 1.74% monoclonal antibody fragments at solution pH of 4.0, 5.0, 6.0, 7.0, 8.0, or 9.0 having a solution conductivity of 4.5 mS/cm or 22 mS/cm. The different solutions are subsequently treated with activated carbon under static binding conditions, as described below.

Preparation of the MAB II fragment spiked solutions began by digesting a portion of the monoclonal antibody with papain enzyme to produce the fragments. After digestion, the enzyme is inactivated by adding a solution of 0.3 M iodoacetate. The papain digested monoclonal antibody solutions are dialyzed into water with dialysis tubing (Standard RC Dialysis Trial Kits, Spectra/Por 1-3, 3.5K MWCO, 54 mm FLAT WIDTH, serial number: 132725. Spectrum Laboratories, Inc. Rancho Dominguez, Calif., 90220 USA) to remove buffer salts. The dialysis tubing is loaded with approximately 0.15 L of the papain digested monoclonal antibody solution and submerged in 4.0 L of water for 24 hours. The dialysis tubing is then moved into a new container with 4.0 L of fresh water where it remains submerged for an additional 24 hours.

The stock solution of fragment spiked MAB II is prepared by combining 144 mL of MAB III solution in water, 36 mL of papain digested MAB II in water, and 18 mL of 250 mM Tris base. The solution is adjusted to pH 9.0 with the addition of 1.8 M Tris base. The solution is filtered through a 0.22 μm membrane (Stericup-GP 0.22 μm Millipore Express PLUS membrane, 250 mL, catalogue number: SCGPU02RE, EMD Millipore Corporation, Billerica, Mass., 01821, USA). The resulting solution has a conductivity of 4.5 mS/cm. 4.0 M sodium chloride is added to a portion of the fragment spiked MAB II solution at pH 9.0, until the solution conductivity reaches 22 mS/cm.

The pH of a portion of the pH 9.0 fragment spiked MAB II solution at 4.5 mS/cm or 22 mS/cm is then decreased to pH 8.0 by the addition of 3.0 M acetic acid. The pH of a portion of these solutions at pH 8.0 is then decreased to pH 7.0 by the addition of 3.0 M acetic acid. The pH of a portion of these solutions at pH 7.0 is decreased to pH 6.0 by the addition of 3.0 M acetic acid. The pH of a portion of these solutions at pH 6.0 is then decreased to pH 5.0 by the addition of 3.0 M acetic acid. The pH of a portion of these solutions at pH 5.0 is decreased to pH 4.0 by the addition of 3.0 M acetic acid. Accordingly, using this method, twelve solutions of the fragment spiked MAB II solution at pH 4.0, 5.0, 6.0, 7.0, 8.0 or 9.0 with a conductivity of 4.5 mS/cm or 22 mS/cm are obtained. The fragment spiked MAB II solutions contains 6.38-7.44 mg/mL of MAB II and 1.5-1.7% of fragments.

15 mL centrifuge tubes for each solution pH and conductivity are loaded with 20 mg of Nuchar HD activated carbon (MeadWestVaco Corporation, Richmond, Va., USA). An additional set of 15 mL centrifuge tubes are used as controls and no media is added. To each tube is added 5.0 mL of fragment spiked MAB II stock solution with the appropriate pH and conductivity. The tubes are allowed to rotate for 24 hours and the samples are subsequently filtered through a 0.22 micron membrane (Millex Syringe Filter Units, Millex-GV, 0.22 μm, PVDF, 33 mm, gamma sterilized, catalogue number: SLGV033RB, EMD Millipore Corporation. Billerica, Mass., 01821, USA) to remove any activated carbon particles that might remain suspended in solution. The concentration of MAB II remaining in the samples is determined by UV spectrophotometer at 280 nm. The percentage of fragments remaining in the samples is determined by size exclusion chromatography (SEC).

Figure 4:
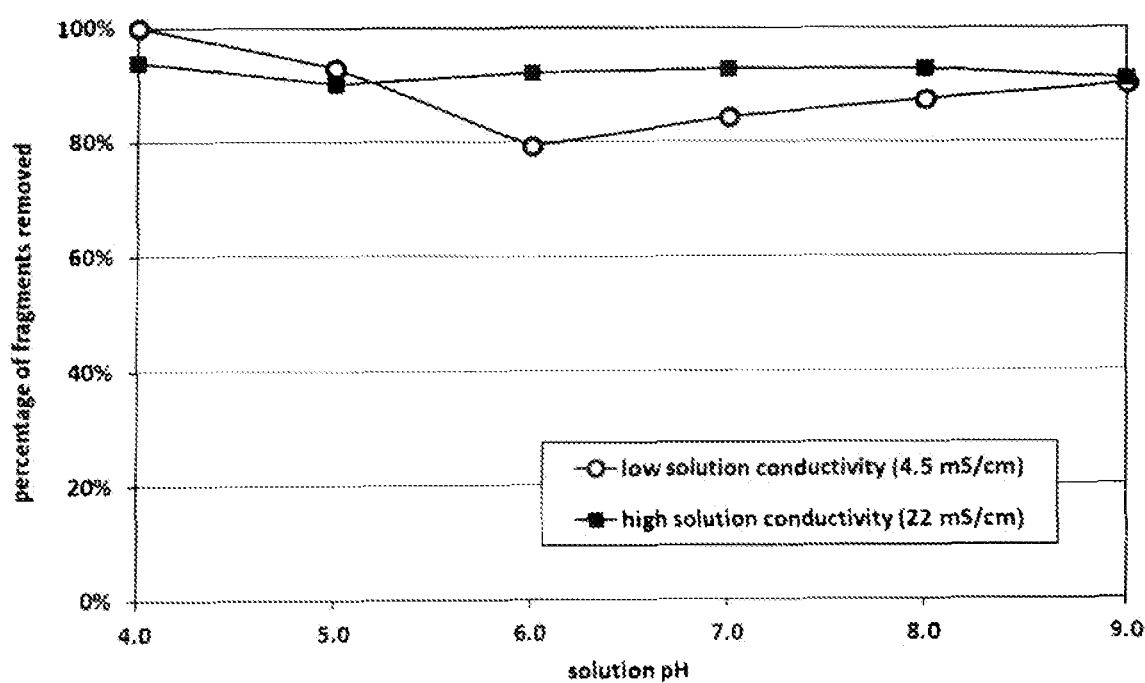
FIG. 4 is a graph depicting the results of a representative experiment to demonstrate the removal of monoclonal antibody fragments from a solution of monoclonal antibody over solution pHs ranging from 4.0 to 9.0 at both low and high solution conductivities by treatment with activated carbon under static binding conditions. The fragment spiked MAB II solutions at pH 4.0, 5.0, 6.0, 7.0, 8.0, or 9.0 that were treated with activated carbon contained 6.38-7.44 mg/mL of MAB II and 1.5-1.7% of fragments, at both low and high conductivities. The X-axis depicts the solution pH and the Y-axis depicts the percentage of fragments removed from the monoclonal antibody solution calculated by subtracting the percentage of fragments in the treated solution divided by the percentage of fragments in the untreated solution from 100%.

As summarized in Table VII and FIG. 4, this experiment demonstrates that monoclonal antibody fragments can be selectively removed using activated carbon from a monoclonal antibody solution over a wide range of pH from 4.0 to 9.0 at both low and high solution conductivities.

TABLE VII

Recovery of monoclonal antibody and percentage of fragments after static treatment of MAB II solution with activated carbon over a pH range of 4.0 to 9.0 at both low and high solution conductivities.

| solution pH | conductivity (mS/cm) | activated carbon (mg) | antibody recovery | percentage of fragments |
|---|---|---|---|---|
| 4.0 | 4.5 | 0 | — | 1.50% |
| 4.0 | 4.5 | 20 | 95% | 0.00% |
| 4.0 | 22 | 0 | — | 1.49% |
| 4.0 | 22 | 20 | 91% | 0.09% |
| 5.0 | 4.5 | 0 | — | 1.70% |
| 5.0 | 4.5 | 20 | 89% | 0.12% |
| 5.0 | 22 | 0 | — | 1.52% |
| 5.0 | 22 | 20 | 87% | 0.15% |
| 6.0 | 4.5 | 0 | — | 1.69% |
| 6.0 | 4.5 | 20 | 89% | 0.35% |
| 6.0 | 22 | 0 | — | 1.54% |
| 6.0 | 22 | 20 | 93% | 0.12% |
| 7.0 | 4.5 | 0 | — | 1.53% |
| 7.0 | 4.5 | 20 | 96% | 0.24% |
| 7.0 | 22 | 0 | — | 1.52% |
| 7.0 | 22 | 20 | 97% | 0.11% |
| 8.0 | 4.5 | 0 | — | 1.74% |
| 8.0 | 4.5 | 20 | 95% | 0.22% |
| 8.0 | 22 | 0 | — | 1.68% |
| 8.0 | 22 | 20 | 95% | 0.12% |
| 9.0 | 4.5 | 0 | — | 1.72% |
| 9.0 | 4.5 | 20 | 97% | 0.17% |
| 9.0 | 22 | 0 | — | 1.69% |
| 9.0 | 22 | 20 | 94% | 0.15% |

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of reducing the amount of antibody fragments in a sample comprising an antibody to be purified, the method comprising the steps of:
    (a) providing a sample comprising an antibody and antibody fragments, wherein the fragments are in an amount equal to or greater than at least 0.2% of the amount of the antibody,
    (b) contacting the sample with activated carbon, wherein the activated carbon binds the antibody fragments,
    (c) removing the activated carbon from the sample, thereby resulting in reducing the amount of fragments in the sample.

2. The method of claim 1, wherein the fragments bind Protein A.

3. The method of claim 1, wherein the fragments do not bind Protein A.

4. The method of claim 1, wherein the sample is an eluate collected from a Protein A affinity chromatography column.

5. The method of claim 1, wherein activated carbon is packed in a column, a pod, a cartridge, or a capsule.

6. The method of claim 5, wherein the activated carbon is packed in a column and the column residence time is from 15 seconds to ten minutes.

7. The method of claim 1, wherein the wherein the fragments are in an amount equal to or greater than at least 0.5% of the amount of the antibody.

8. The method of claim 1, wherein the fragments are in an amount equal to or greater than at least 1% of the amount of the antibody.

9. The method of claim 1, wherein the fragments are in an amount equal to or greater than at least 2% of the amount of the antibody.

10. The method of claim 1, wherein the activated carbon is removed using filtration or centrifugation or a combination thereof.

11. The method of claim 1, wherein the purity of the antibody in the sample is increased following a reduction in the amount of fragments.

12. The method of claim 11, wherein the purity of the antibody is increased by at least 10%, or at least 20%, or at least 30%, or at least 40%, or at least 50%, or more.

* * * * *